US006929126B1

(12) United States Patent
Herbert

(10) Patent No.: US 6,929,126 B1
(45) Date of Patent: Aug. 16, 2005

(54) SYRINGE DISPOSAL DEVICE

(75) Inventor: John Herbert, St. Ives (AU)

(73) Assignee: Baske Pty Ltd., Sydney (AU)

( * ) Notice: Subject to any disclaimer, the term of this patent is extended or adjusted under 35 U.S.C. 154(b) by 67 days.

(21) Appl. No.: 10/089,398

(22) PCT Filed: Oct. 2, 2000

(86) PCT No.: PCT/AU00/01204

§ 371 (c)(1),
(2), (4) Date: Jul. 15, 2002

(87) PCT Pub. No.: WO01/23019

PCT Pub. Date: Apr. 5, 2001

(30) Foreign Application Priority Data

Sep. 30, 1999 (AU) .................................... PQ3204

(51) Int. Cl.[7] .............................................. B65D 83/10
(52) U.S. Cl. ...................................... 206/365; 206/438
(58) Field of Search ............................... 206/364–367, 206/438

(56) References Cited

U.S. PATENT DOCUMENTS

| 3,342,319 | A | * | 9/1967 | Faulseit ...................... 206/365 |
| 4,892,525 | A | * | 1/1990 | Hermann, Jr. et al. ...... 604/263 |
| 4,954,239 | A | * | 9/1990 | Mueller ...................... 206/571 |
| 5,417,326 | A | * | 5/1995 | Winer ......................... 206/365 |
| 5,451,213 | A | * | 9/1995 | Teicher et al. .............. 604/192 |
| D364,501 | S | * | 11/1995 | Gough ......................... D3/203 |
| 5,519,931 | A | * | 5/1996 | Reich ......................... 29/426.3 |
| 5,611,429 | A | * | 3/1997 | Phillips ...................... 206/365 |
| 5,828,073 | A | * | 10/1998 | Zhu et al. ................. 250/506.1 |
| 6,186,325 | B1 | * | 2/2001 | Schmidt et al. ............. 206/364 |

FOREIGN PATENT DOCUMENTS

| FR | 2650511 | 2/1991 |
| WO | WO 99/26680 | 6/1999 |

* cited by examiner

Primary Examiner—Shian T. Luong
(74) Attorney, Agent, or Firm—Sheridan Ross PC

(57) ABSTRACT

Disclosed is a syringe disposal device (10) suitable for disposal of a single syringe. The device is suitable for disposal of syringes (30) having a needle (33), a barrel (38), a plunger (39) and on the barrel (38) or plunger (39), a transversely extending flange portion (38a). The disposal device (10) may include a needle encapsulating portion (12), a syringe barrel encapsulating portion (14) and a syringe retention portion (16). The syringe retention portion (16) has an open end (18) to allow syringe (30) to be inserted into device (10). The opposed end (19) of syringe retention portion (16) communicates the retention portion (16) with syringe barrel encapsulating portion (14). Engagement means (20) are provided at, or proximate, the opposed end (19) of the syringe retention portion (16) for retaining syringe (30) within the disposed device (10) after passage of the transversely extending flange (38a) past the engagement means (20) by interference fit. The disposal device (10) is advantageously of tapered form.

8 Claims, 7 Drawing Sheets

SYRINGE DISPOSAL DEVICE

FIELD OF INVENTION

This invention relates to a syringe disposal device and, in particular, to a device suitable for encapsulation and disposal of a single syringe.

PRIOR ART

The hazards of used needles are now well recognised. It is well known that a number of diseases may be transmitted by reuse of syringes. For example, the transmission of AIDS and Hepatitis viruses such as Hepatitis C through reuse of needles is now well documented.

Transmission of disease is not only possible through reuse of needles but indeed may be caused by so called needle stick injury in which a needle inadvertently punctures the skin of a person allowing transmission of a virus to that person. A number of proposals for dealing with such hazards have been documented in the patent literature.

For example, French Patent No. 2650511 describes a syringe protection device which is intended to facilitate preparation of injections. The device is also intended to eliminate the risk of pricking injuries as well as the possible recovery of the used syringes.

Most such proposals are predicated on use in a therapeutic environment in which many needles are used on a daily basis and a centralised disposal unit may readily be used for the purpose of needle disposal. In such environments, the risk of reuse is relatively small and the prime concern is to ensure that disease transmission through needle stick injury does not occur. A number of technologies for needle destruction and/or containment are known. Grinding, melt-fusion and other technologies are available which confine used needles in a safe environment subsequent to other disposal steps.

Real hazards remain, however in the non-therapeutic environment where availability of a centralised needle disposal system is problematic. Even if such disposal facility is available there remains the problem that accidents may occur while conveying a used needle to the disposal facility. It is understood that while there has been a dramatic increase in the number of syringes distributed and collected from disposal units with different sharps containers, surveys have indicated that a major problem with needle syringe exchange programs is availability of disposal units on both a locality and time frame basis.

Therefore, it is in the interest of public health for more needle disposal options to be available to drug users to minimize hazards to the general community through disease transmission as above described. Such disposal options should be suitable for safe disposal of single syringes after a single use. In that way, the disposal system interfaces well with the needle exchange program.

SUMMARY OF THE INVENTION

It is the object of the current invention to provide a syringe disposal device which addresses the problems above described at reasonable cost and accessibility to the drug user.

With this object in view, the present invention provides a syringe disposal device suitable for disposal of a single syringe having a needle, a barrel, a plunger and, on the barrel or plunger, a transversely extending portion, the disposal device including;

a.) a needle encapsulating portion;
b.) a syringe barrel encapsulating portion; and
c.) a syringe retention portion;
wherein said syringe retention portion has an open end for insertion of a syringe therein and an opposed end communicating said retention portion with said syringe barrel encapsulating portion, engagement means being provided at or proximate, said opposed end of said syringe retention portion for retaining a syringe within the disposal device after passage of said transversely extending portion past said engagement means by an interference fit.

The disposal device may advantageously have a body of tapered form. In particular, the syringe retention portion may advantageously be tapered. The syringe retention portion may have greater external dimension along substantially its whole length than an outer diameter of the syringe barrel encapsulating portion and the needle encapsulating portion.

Engagement means additional to those provided in the syringe retention portion may be provided as described, for example, below.

The transversely extending portion may be constituted by a syringe barrel outer surface or a surface of a transversely extending portion of a flange of the plunger or syringe barrel or both. It will ordinarily be constituted by the broadest portion of the disposed syringe thus bearing on the engaging means to prevent syringe retraction by exertion of reasonable force after use.

A number of lug engagement means may be provided for engaging the transversely extending bearing portion. Alternatively, an engaging face of generally annular shape may be provided at the opposed end of the syringe retention portion. Interference fitting or press fitting past the engaging means provides greater assurance that the syringe will be retained within the disposal device following use. To this end, it is preferred that a rigid material is used for fabrication of the device. A suitable rigid polymer is preferably to be used for this purpose, noting that such polymer should have nature requisite to, and fabricated for preventing needle puncture.

The disposal device may incorporate a morse taper, particularly at the transition between the syringe barrel encapsulating portion and the needle encapsulating portion. This accommodates the needle carrier, hub, needle and/or upper end of the syringe barrel in a neat engaging fit similar to that employed for fitting of sockets and the like in tool kits.

The disposal device may be designed such that at least one of the needle encapsulating portion and the syringe barrel encapsulating portion have a multi-stepped configuration for increasing the probability of the needle impacting the inner surface during retaining of a syringe for disposal thereof. A disposal device of this design is described in the Applicant's co-pending Australian Provisional Patent Application No. PQ6999, "Syringe Retaining Device", filed 18 Apr. 2000, the contents of which are hereby incorporated herein by reference.

The syringe disposal unit is suitable for disposal of a syringe following an injection event, especially in a non-therapeutic environment.

In another aspect of the invention, the syringe disposal device may be retained in a holder which includes a syringe, and may include accessories for use in an injection. Such accessories may include distilled water or other solvent for an injectable to be used in the injection and other equipment, such as spoons, for injection preparation. A spoon or receptacle of preferred type may have a wall defining a vessel in which an injectable solution may be prepared, there being provided in the wall a depression forming a sump to which injectable solution drains during drawing up of the injectable solution into an injection device. Such a receptacle is described in Australian Provisional Patent Application No. PQ7000, "Intra-Venous Injection Preparation Device and Kit", filed 18 Apr. 2000, the contents of which are hereby incorporated by reference.

Such a holder should likewise be fabricated from a low cost polymeric or metallic material. If the syringe is provided with the holder, the syringe may be located within the disposal device but in a non-engaged position such that withdrawal of the syringe from the device is readily possible.

Such kits may be produced to have different combinations of contents and may be colour coded to indicate the nature of their contents such that users may readily be informed of suitable packaged holders for their use.

Such kits would be readily available from pharmacies in a package that facilitates anonymity of the transaction. This will greatly reduce discomfort to both the pharmacist and the intravenous drug user in a transaction carried out in a busy pharmacy. Reduction in barriers such as this at the pharmacy-intravenous drug user level is important to adoption of safe disposal devices of the kind offered by this invention. In so doing, ready availability of such disposal devices and kits may be assured. User of the disposal device and the kit generally will also reduce the risk of cross-infection between used and clean syringes.

BRIEF DESCRIPTION OF THE DRAWINGS

The invention will be more fully understood from the following description made with reference to the following drawings in which.

DETAILED DESCRIPTION OF PREFERRED EMBODIMENTS

Figure 1:
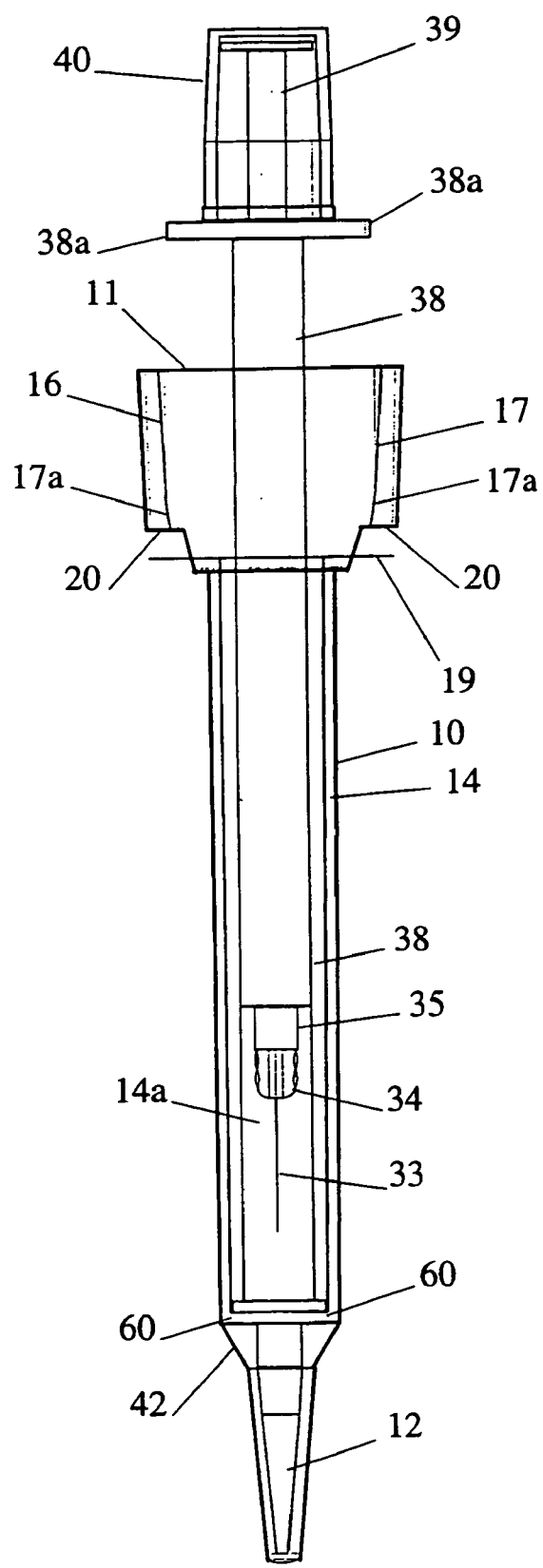
FIG. 1 shows a side section of a syringe disposal device in accordance with the invention having a syringe with the syringe in a non-engaged position.

Referring to FIG. 1 of the drawings, there is shown the syringe disposal device 10 of the present invention fabricated from a rigid polymeric material. The syringe disposal device 10 includes a needle encapsulating portion 12, a syringe barrel encapsulating portion 14 and a syringe retention portion 16. The plunger retention portion 16 has a tapered internal wall 17 and it will be observed that said accommodating portion 16 has greater diameter along substantially its whole length than an outer diameter of the syringe barrel encapsulating portion 14 and needle encapsulating portion 12.

The disposal device 10 is suitable for disposing of any kind of syringe. The syringe 30 shown in FIG. 1 and the drawings generally is of a conventional type having a needle 33, a hub 34, a needle carrier 35, a barrel 38 and a plunger 39. The barrel 38 has transversely extending flange portions 38a which, on engagement with the engaging means 20, retain the syringe 30 within disposal device 10.

The syringe retention portion 16 has an open end 18 to allow syringe 30 to be placed by pressing into the device 10. Particularly, it is of sufficient lateral dimension to amply accommodate barrel 38 flanges 38a at open end 11, thus assisting with location. At another opposed end 19, retention portion 16 communicates with the syringe barrel encapsulating portion 14. The opposed end 19, of circular or oval shape, is provided with engagement means 20 retaining a syringe 30 within the disposal device 10 after passage of a flange portions 38a past engaging means 20 by interference fitting.

Figure 5:
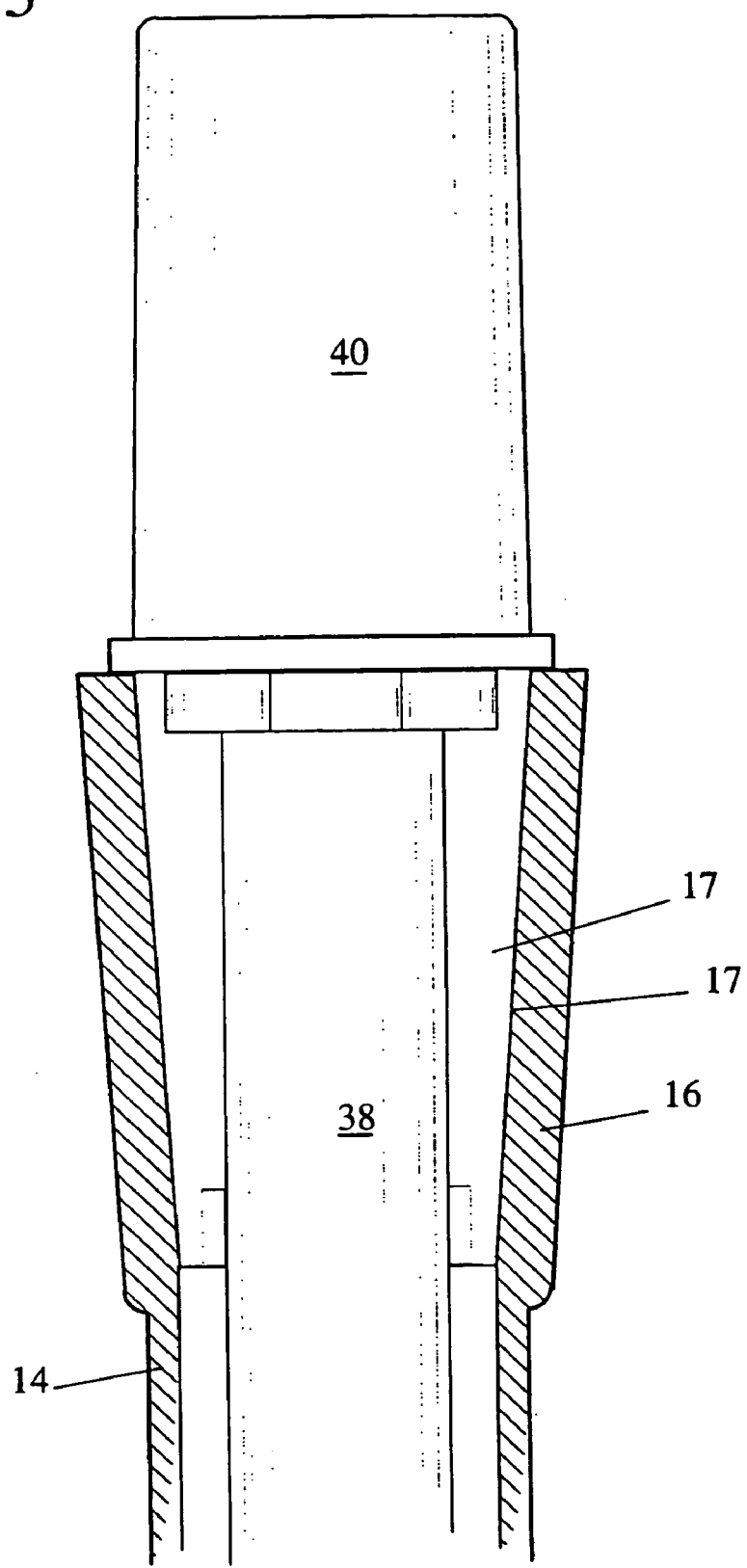
FIG. 5 shows the section of FIG. 3 with a syringe needle cover cap in place on the syringe maintaining it in a non-engaged position.
Figure 6:
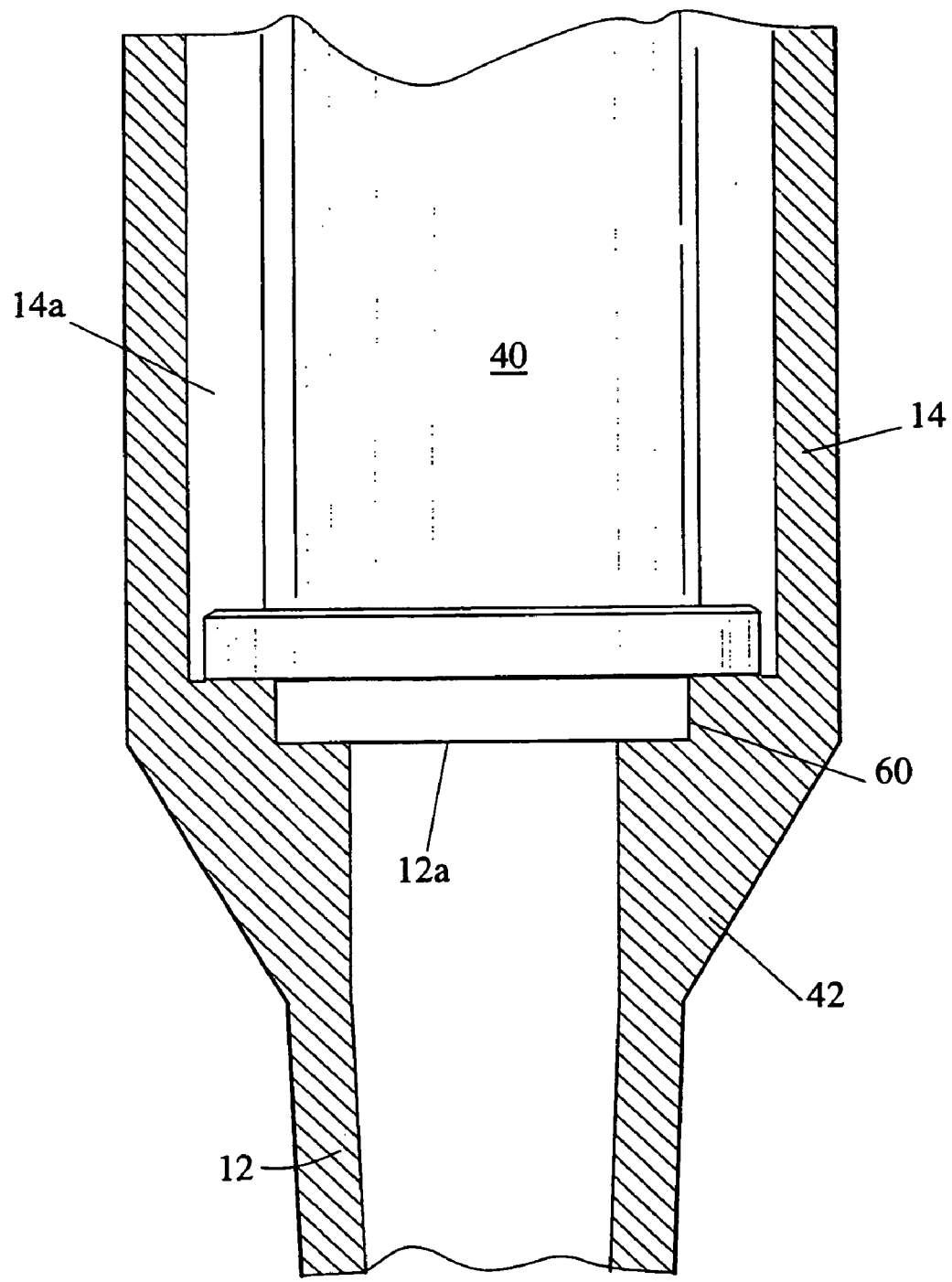
FIG. 6 shows a capped syringe preventing it being engaged in the syringe disposal device in accordance with a further embodiment of the present invention.

In FIGS. 1 and 5, the syringe 30 is shown in a non-retained position as may be suitable prior to an injection and readily accommodated by the inventive device. It will be noted, in this case, that location of cap 40 at the end of plunger 39 remote from needle encapsulating portion 12 prevents insertion of the syringe past the engaging means 20 because the cap 40 is of greater width than a lateral dimension of opposed end 19. The syringe 30 can therefore not be retained within the disposal device 10 until cap 40 is removed. FIG. 6 shows another example of a cap 40 fitted at the needle end of syringe 30 used to prevent syringe 30 being placed into engagement with disposed device 10 until necessary. Here, cap 40 has greater width than an opening 12a of needle encapsulating portion 12. The syringe 30 is thus prevented from moving into an engaged position within device 10. Other arrangements to prevent this result are possible.

Figure 2:
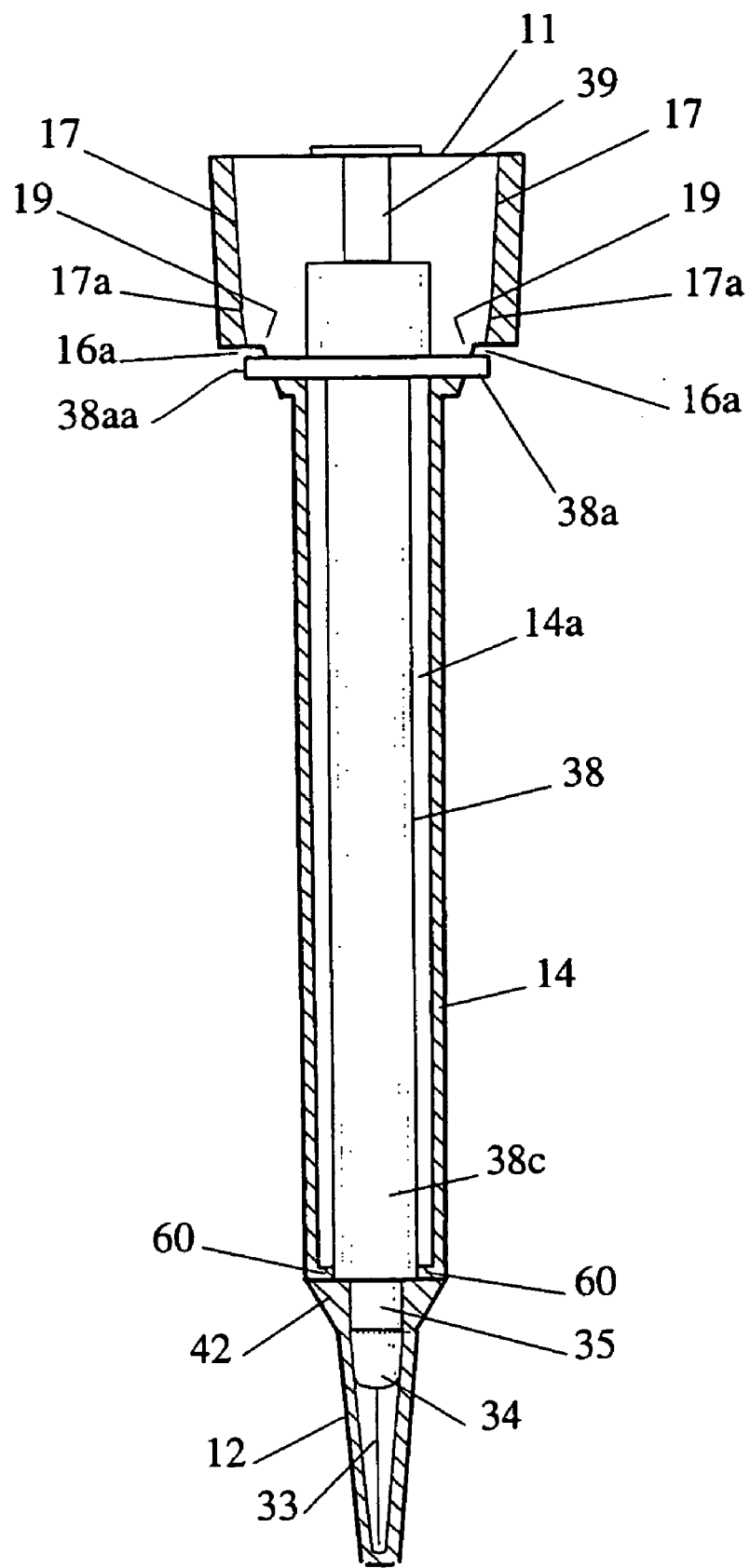
FIG. 2 shows a side section of a syringe disposal device in accordance with the invention having a syringe in an engaged position.

Referring now to FIG. 2, there is shown syringe 30 in a disposed position retained within disposal device 10. In this case, a user of the disposal device 10 has press or interference fitted syringe 30 past the engaging means 20 into cavity 14a of barrel encapsulating portion 14. In particular, it will be seen that transversely extending flange portion 38a of barrel 38 has been pressed past engaging means 20 to retain the syringe 30 within the disposal device 10.

Figure 3:
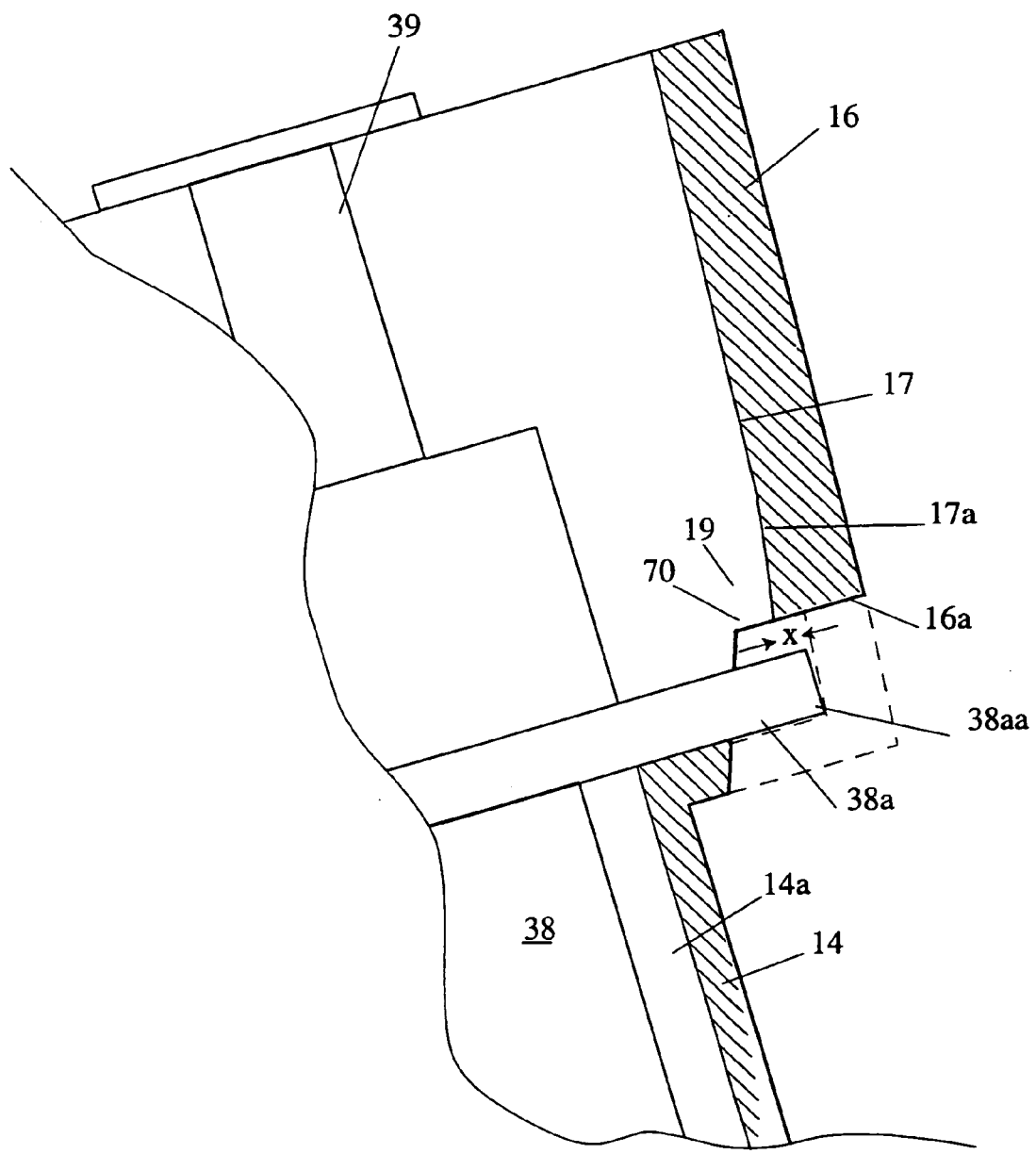
FIG. 3 shows a detail section showing retention of a syringe flange within the syringe disposal device of the present invention.

Press or interference fitting is achieved in the following manner. The diameter of the transversely extending flange portion 38a of the syringe barrel 38 is slightly greater by a distance, x, than the diameter of opposed end 19 of syringe retention portion 16 as conveniently shown in FIG. 3. Thus, as the user presses syringe 30 through the retention portion 16, the outermost surface 38aa of the transversely extending flange 38a starts to interfere with an inner surface 17a of the wall 17 of retention portion 16 adjacent opposed end 19. Thus surfaces 38aa and 17a form one part of engaging means 20. Pressure exerted by the user causes the wall 17a to deform allowing the syringe 30 to be pressed further into disposal device 10.

After press fitting, retraction of the syringe 30 by reasonable force is prevented by an annular engaging face 16a bearing on flange portions 38a. It will be noted that the syringe disposal device 10 has a slot 70 formed in its wall 14a proximate engaging face 16a, forming the remaining portion of engaging means 20, through which an outer portion of flange portion 38a extends in the engaged position. This slot 70 need not penetrate the external wall of retention portion but may be formed internally thereof, as shown by the dashed outline indicating a continuous external wall. The disposal device 10 may be designed such that flange portion 38a seals the syringe barrel 38 encapsulating portion 14 and this minimises risk of harmful fluids coming into contact with a user of disposal device 10.

The disposal device 10 is conveniently manufactured from a rigid polymeric material. This is not to preclude fabrication from other materials, but use of a substantially rigid material of fabrication tends to promote efficacy of interference fitting and is preferred for use in this device 10. It is not intended that the engaging means 20, as formed by opposed end 19, wall portion 17a, engaging surface 16a and flange portion 38aa be substantially flexible as retraction of syringe 30 then becomes a real danger. The polymeric material must have sufficient stiffness to prevent puncture by needle 33. Polyamide polymers, such as nylons, may be most suitable for this application. One example of a nylon is that polymer sourced under the trade mark ZYTEL, a Registered Trade Mark of Dupont.

It is not necessary that it be the transversely extending flange portion 38a of the syringe 30 that passes the engaging surface 16a.

Another portion of the syringe 30 may alternatively or additionally be engaged and this may be necessary for syringes of other design. Further, other forms of engaging means may be contemplated by the present invention. For example discrete lugs could be used rather than an annular engaging surface.

Otherwise, the transversely extending portion may be formed by a syringe barrel 38 outer surface or indeed any other appropriate surface of the syringe 30. It is contemplated that the disposal device 10 will be suitable for disposal of all conventional designs of syringe as, in this way, efficacy of disposal device 10 will be best promoted.

Figure 4:
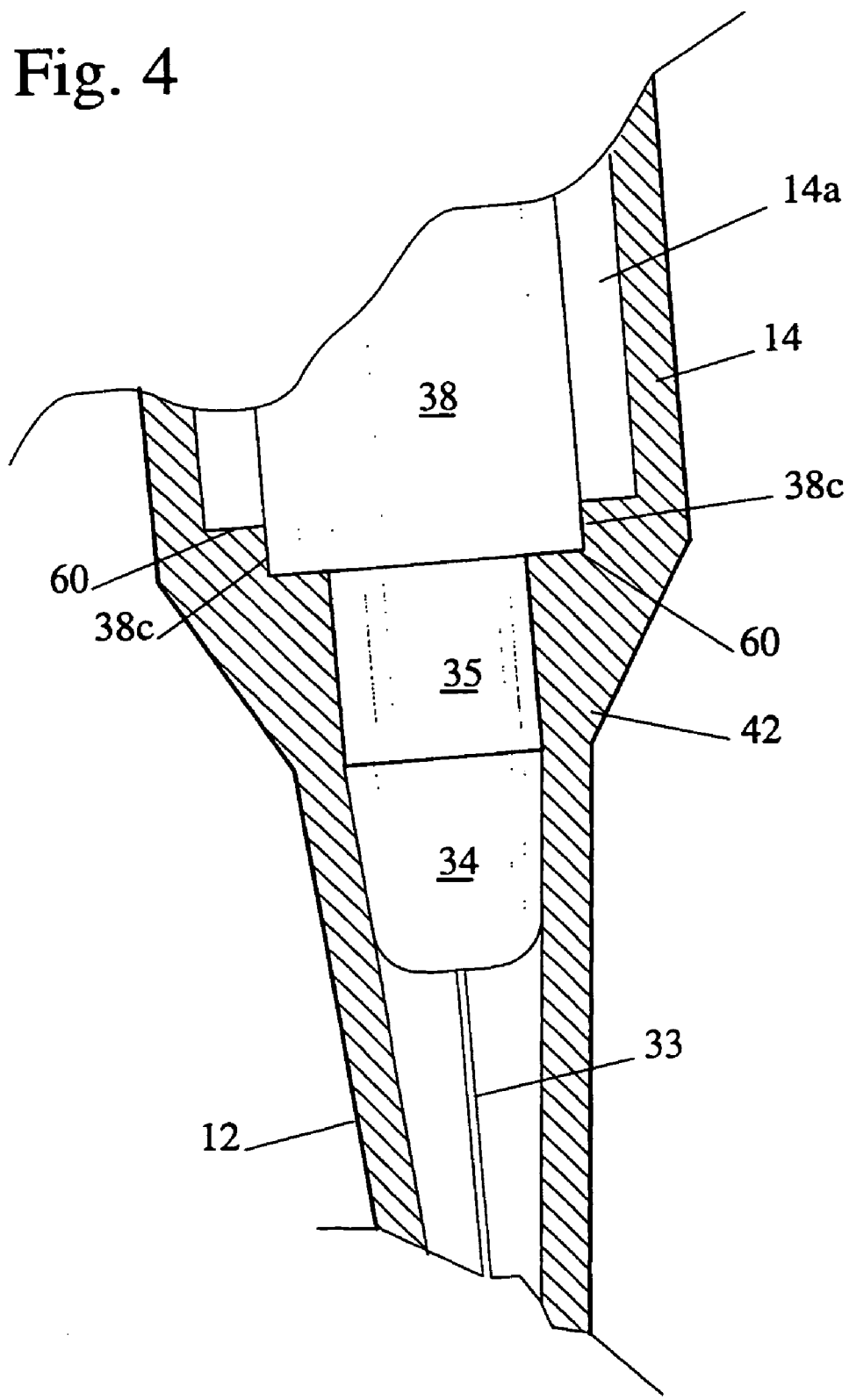
FIG. 4 shows a part section view showing a portion of the syringe barrel encapsulating portion and the needle encapsulating portion of a syringe disposal device in accordance with the present invention.

It will be observed that when syringe 30 is properly retained within the device 10, a lower end of the syringe barrel 38c, the needle carrier 35 and hub 34 are retained by light press fit within a morse taper 60 formed at the transition 42 between the syringe barrel encapsulating portion 14 and the needle encapsulating portion 12 as conveniently shown in FIG. 4. Indeed, when the lower end 38c of the syringe barrel 38 comes into contact with morse taper 60, this will inform the intravenous drug user that the syringe 30 is safely stored within disposal device 10. A clicking sound generated by passage of transversely extending flange portion past sealing surface 16a and wall portion 17a at opposed end 19 of retention portion 16 provides further indication that the syringe 30 is safely stored out of harm's way.

The morse taper 60 may be designed in an effort to achieve needle 33 destruction as described in the Applicant's co-pending Australian Provisional Patent Application PQ6999, filed 18 Apr. 2000, the contents of which are hereby incorporated by reference.

Another feature of the morse taper 60 will be observed. Because the lower end 38c of the syringe barrel 38 and needle 33 is safely sealed within morse taper 60, injectable fluids will not leak back where they may cause harm. It is to be noted that the needle encapsulating portion 12 must be formed of material sufficiently rigid to avoid any possibility of needle 33 puncturing it. If such puncture were possible, the efficacy of the disposal device 10 would be unacceptable. Polymeric materials may be selected to achieve this purpose as described above.

Figure 7:
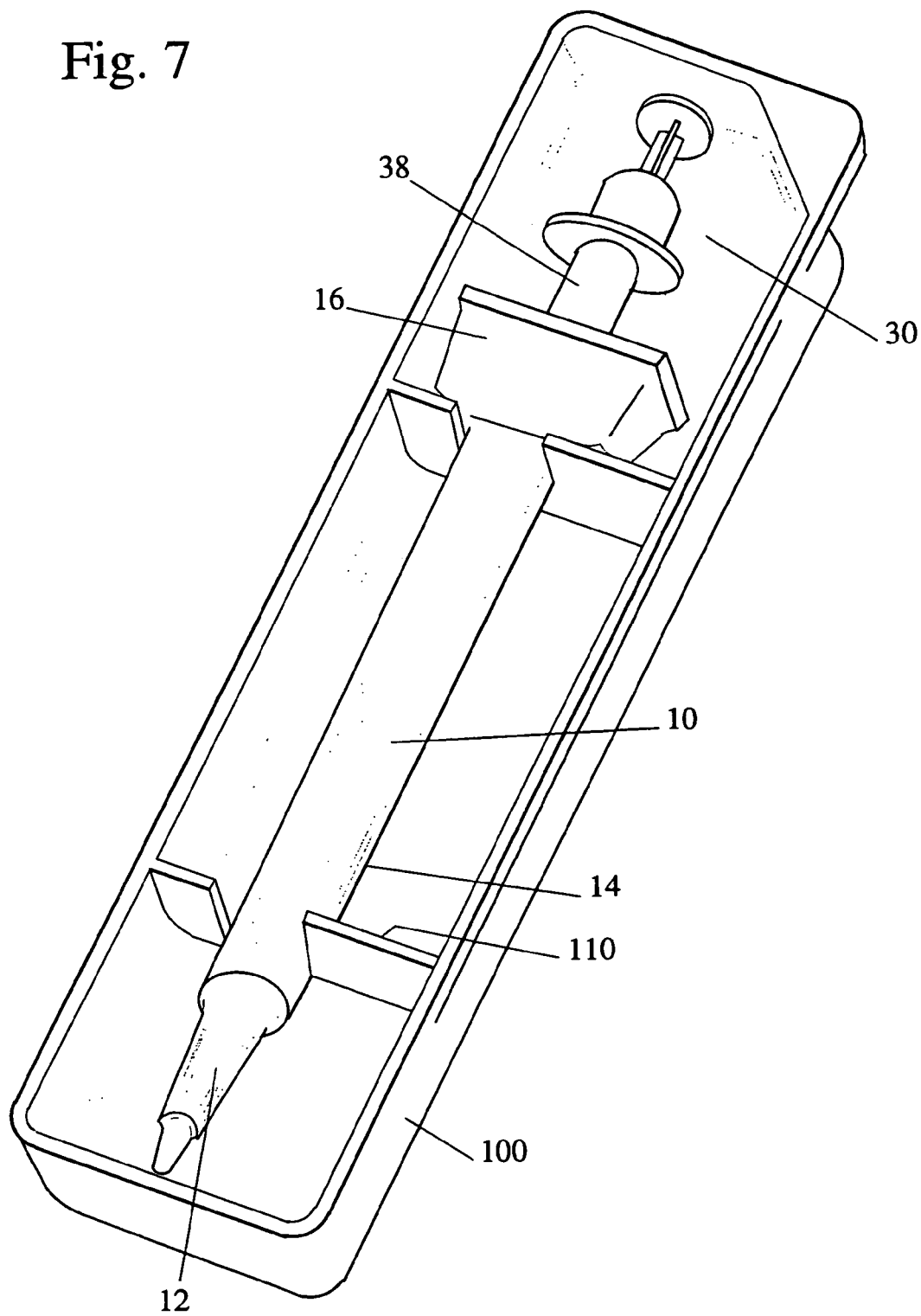
FIG. 7 shows a holder for the syringe disposal device in accordance with a further aspect of the present invention.

Referring now to FIG. 7, the syringe disposal device 10 may conveniently be packed in an injection moulded holder 100, with a removable transparent or foil wrapper which may be printed with indicia about the device. Packaging equipment may be designed to effect this purpose. In such case, the wrapper must be sealed to the holder at sufficient pressure to maintain the seal, at least 20 kPa, more preferably 50 kPa or more. A reclosable lid could be provided. Holder 100 contains suitable items for an injection event in its thermo-formed or injection moulded base 110 which neatly accommodates syringe disposable device 10. Ordinarily, the holder 100 will not contain the injectable but this may be provided if desired and permitted. The holder 100 can further contain a spoon for mixing the injectable with distilled water prior to injection as well as filters and distilled water. The holder 100 may be packaged to be sterile prior to opening by the user and in this way, the injection event may be made as safe as possible. It is most advantageous that the holder 100 accommodate a single syringe 30 as it is most likely that this will be the preferred capacity of needle exchanges for legal reasons. In any event, construction of the device 10 in a simple inexpensive way makes it possible to minimise the cost of such single use holders 100.

Holders 100 may be disposed of as desired by the user but could be collected in a central disposal area. A condition of needle exchange may be return of the holders 100. In any event, if the device is properly used, the public health risks posed by the use of syringe 30 are much reduced.

Modifications and variations may be made to the present invention after reading of the disclosure by a skilled reader. Such modifications and variations are intended to form part of the present invention. For example, a cover may be provided for device 10 at its open end for purposes of sterility. The barrel encapsulating and needle encapsulating portions may be integrated into one portion.

What is claimed is:

1. A syringe disposal device suitable for disposal of a single syringe having a needle having a hub, a barrel, a plunger and, on the barrel or plunger, a transversely extending portion, the disposal device including: a needle encapsulating portion;
   a syringe barrel encapsulating portion; and
   a syringe retention portion, wherein said syringe retention portion, having greater external dimension along substantially its whole length than an outer diameter of the syringe barrel encapsulating portion and the needle encapsulating portion, has an open end for insertion of a syringe therein and an opposed end communicating said retention portion with said syringe barrel encapsulating portion, engagement means being provided at or proximate, said opposed end of said syringe retention portion for retaining a syringe within the disposal device after passage of said transversely extending portion of the syringe barrel or plunger past said engagement means by interference fit;
   a morse taper for engaging the needle hub at a transition between said syringe barrel encapsulating: portion and said needle encapsulating portion.

2. The syringe disposal device according to claim 1 wherein the syringe retention portion is tapered and has greater external dimension along substantially its whole length than an outer diameter of the syringe barrel encapsulating portion and the needle encapsulating portion.

3. The syringe disposal device of claim 1 wherein said engagement means is a lug engagement means for engaging said transversely extending portion after passage thereof past said lug engagement means.

4. The syringe disposal device of claim 1 wherein said engagement means is an annular engaging face provided at said opposed end of said syringe retention portion.

5. The syringe disposal device of claim 1 wherein said device is of tapered form.

6. A kit including a holder for retaining a syringe disposal device as claimed in claim 1 and said syringe disposal device.

7. A syringe disposal device suitable for disposal of a single syringe having a needle having a hub, a barrel, a plunger and, on the barrel or plunger, a transversely extending portion, the disposal device including;
   (a) a needle encapsulating portion;
   (b) a syringe barrel encapsulating portion;
   (c) a syringe retention portion, having greater external dimension along substantially its whole length than an outer diameter of the syringe barrel encapsulating portion and the needle encapsulating portion, has an open end for insertion of a syringe therein and an opposed end communicating said retention portion with said syringe barrel encapsulating portion; and
   (d) engagement means being provided at or proximate, said opposed end of said syringe retention portion for retaining a syringe within the disposal device after passage of said transversely extending portion of the syringe barrel or plunger past said engagement means by interference fit wherein a morse taper is located at a transition between said syringe barrel encapsulating portion and said needle encapsulating portion.

8. A syringe disposal device suitable for disposal of a single syringe having a needle having a hub, a barrel, a plunger and, on the barrel or plunger, a transversely extending portion, the disposal device including;
   (a) a needle encapsulating portion;
   (b) a syringe barrel encapsulating portion; and
   (c) a syringe retention portion;
   having greater external dimension along substantially its whole length than an outer diameter of the syringe barrel encapsulating portion and the needle encapsulating portion, has an open end for insertion of a syringe therein and an opposed end communicating said retention portion with said syringe barrel encapsulating portion wherein lug engagement means is provided at or proximate, said opposed end of said syringe retention portion for engaging said transversely extending portion of said syringe and retaining it within the disposal device after passage of said transversely extending portion of the syringe barrel or plunger past said lug engagement means by interference fit and wherein a morse taper is located at the transition between said syringe barrel encapsulating portion and said needle encapsulating portion.

* * * * *